(12) United States Patent
Steinhauser et al.

(10) Patent No.: US 10,887,492 B2
(45) Date of Patent: Jan. 5, 2021

(54) TEMPORAL ALIGNMENT OF AND SIGNAL-TO-NOISE-RATIO ENHANCMENT IN IMAGE STREAMS FOR MULTI-CHANNEL X-RAY IMAGING

(71) Applicant: KONINKLIJKE PHILIPS N.V., Eindhoven (NL)

(72) Inventors: Heidrun Steinhauser, Eindhoven (NL); Alexander Johannes Admiraal, Eindhoven (NL); Robin Pieter De Paus, Breda (NL); Markus Johannes Harmen Den Hartog, Eindhoven (NL); Frans Henk Kremer, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 627 days.

(21) Appl. No.: 14/411,949

(22) PCT Filed: Jul. 1, 2013

(86) PCT No.: PCT/IB2013/055393
§ 371 (c)(1),
(2) Date: Dec. 30, 2014

(87) PCT Pub. No.: WO2014/006556
PCT Pub. Date: Jan. 9, 2014

(65) Prior Publication Data
US 2015/0172516 A1 Jun. 18, 2015

Related U.S. Application Data

(60) Provisional application No. 61/668,046, filed on Jul. 5, 2012.

(51) Int. Cl.
*H04N 5/04* (2006.01)
*H04N 13/00* (2018.01)
(Continued)

(52) U.S. Cl.
CPC .............. *H04N 5/04* (2013.01); *A61B 6/022* (2013.01); *A61B 6/4007* (2013.01);
(Continued)

(58) Field of Classification Search
CPC ....... A61B 6/022; A61B 6/4007; A61B 6/466; A61B 6/5229; G06T 11/005;
(Continued)

(56) References Cited

U.S. PATENT DOCUMENTS 5,841,833 A  11/1998  Mazess et al.
6,268,846 B1 *  7/2001  Georgiev .............. G06T 3/0093
                                                345/419

(Continued)

FOREIGN PATENT DOCUMENTS

WO  2010146504 A1  12/2010
WO  2012123843 A1  9/2012

OTHER PUBLICATIONS

Goncalves et al, Structure from Stereo Vision using Unsynchronized Cameras for simultaneous Localization and Mapping, 2005, IEEE, pp. 2993-2998 (Year: 2005).*

(Continued)

*Primary Examiner* — Joon Kwon

(57) ABSTRACT

An apparatus (IP) and a method to generate temporally-aligned image frames for image-streams (LS, RS) in a multi-channel (CR, CL) imaging system (100). The apparatus (IP) allows reducing or removing temporal distance artifacts that occur when processing the frames into combined image material. The apparatus can also be used to improve signal-to-noise ratio of the frames. The multi-channel imaging system (100) may be a stereoscopic imager.

17 Claims, 2 Drawing Sheets

(51) Int. Cl.
*H04N 13/161* (2018.01)
*A61B 6/00* (2006.01)
*A61B 6/02* (2006.01)
*G06T 11/00* (2006.01)
*G06T 7/38* (2017.01)

(52) U.S. Cl.
CPC .............. *A61B 6/5229* (2013.01); *G06T 7/38* (2017.01); *G06T 11/005* (2013.01); *H04N 13/161* (2018.05); *A61B 6/466* (2013.01); *G06T 2207/10021* (2013.01); *G06T 2207/10116* (2013.01)

(58) Field of Classification Search
CPC . G06T 2207/10021; G06T 2207/10116; G06T 7/0038; G06T 7/38; H04N 13/0048; H04N 5/04
USPC ..................................... 348/43, 513
See application file for complete search history.

(56) References Cited

U.S. PATENT DOCUMENTS

| | | | |
|---|---|---|---|
| 6,393,097 B1 | 5/2002 | Aufrichtig et al. | |
| 7,412,031 B2 | 8/2008 | Endo | |
| 7,668,361 B2 | 2/2010 | Spies | |
| 9,014,424 B2* | 4/2015 | Berlinger | G06T 7/251 348/14.01 |
| 2002/0105583 A1* | 8/2002 | Matsutani | H04N 5/357 348/241 |
| 2004/0092811 A1* | 5/2004 | Hill | A61B 6/032 600/413 |
| 2005/0053192 A1* | 3/2005 | Sukovic | A61B 6/022 378/41 |
| 2005/0094869 A1 | 5/2005 | Yoda | |
| 2006/0125920 A1* | 6/2006 | Criminisi | H04N 5/0733 348/159 |
| 2011/0058050 A1* | 3/2011 | Lasang | H04N 5/144 348/208.4 |
| 2011/0199457 A1* | 8/2011 | Yoshida | G02B 27/2264 348/43 |
| 2011/0285815 A1* | 11/2011 | Kervec | H04N 13/0003 348/43 |
| 2012/0008916 A1* | 1/2012 | Lane | G11B 27/034 386/241 |

OTHER PUBLICATIONS

Zhou et al, "Dynamic Depth Recovery From Unsynchronized Video Streams", Proceedings of the IEEE Computer Conference on Computer Vision and Pattern Recognition, vol. 2, Jun. 2003, pp. 351-358.

Schenderlein et al, "Catheter Tracking in Asynchronous Biplane Fluoroscopy Images by 3D B-Snakes", Medical Imaging, vol. 7625, Mar. 2010, pp. 1-8.

Svedman, "3-D Structure From Stereo Vision Using Unsynchronized Cameras", Master's Thesis in Computer Science, Stockholm Sweden, 2005, pp. 1-60.

Matsumoto et al, "Multiview Contraints in Frequency Space and Camera Calibration From Unsynchronized Images", IEE Conference on Computer Vision and Pattern Recognition, Jun. 2010, pp. 1601-1608.

Seki et al, "Simultaneous Optimization of Structure and Motion in Dynamic Scenes Using Unsynchronized Stereo Camers", IEEE Conference on Computer Vision and Pattern Recognition, Jun. 2007, pp. 1-8.

Svedman et al, "Structure From Stereo Vision Using Unsynchronized Cameras for Simultaneous Licalization and Mapping", IEE/RSJ International Conference on Intelligent Robots and Systems, Aug. 2005, pp. 2993-2998.

Aach et al, "Motion-Compensated Defect Interpolation for Flat-Panel Detectors", Institute for Signal Processing and Institute for Neuro- and Bioinformatics, University of Lubeck, pp. 1-12, Undated.

* cited by examiner

TEMPORAL ALIGNMENT OF AND SIGNAL-TO-NOISE-RATIO ENHANCMENT IN IMAGE STREAMS FOR MULTI-CHANNEL X-RAY IMAGING

CROSS-REFERENCE TO PRIOR APPLICATIONS

This application is the U.S. National Phase application under 35 U.S.C. § 371 of International Application Serial No. PCT/IB2013/055393, filed on Jul. 1, 2013, which claims the benefit of U.S. Application Ser. No. 61/668,046, filed on Jul. 5, 2012. These applications are hereby incorporated by reference herein.

FIELD OF THE INVENTION

The present invention relates to image processing apparatuses, to an image processing method, to an image processing system, to a computer program element and to a computer readable medium.

BACKGROUND OF THE INVENTION

Multi-channel imaging systems are known in which streams of images ("frames"), one for each channel, are acquired and processed into processed images which may then be displayed on a screen. Examples of such multi-channel imaging systems are stereoscopic systems where frame streams in two channels are produced and then combined into a 3D (three-dimensional) image to provide for example an interventional radiologist with a 3D representation of a region of interest. However it has been observed that said processed images are frequently suffering from image artifacts.

An artifact correction method is described in U.S. Pat. No. 7,668,361.

SUMMARY OF THE INVENTION

There may be therefore a need for an alternative apparatus to improve operation of multi-channel imaging systems. The object of the present invention is solved by the subject matter of the independent claims where further embodiments are incorporated in the dependent claims. It should be noted that the following described aspect of the invention equally apply to the image processing method, the image processing system, to the computer program element and to the computer readable medium.

According to a first aspect of the invention there is provided an image processing apparatus comprising:
- an input interface for receiving i) through a first channel, first and second frames both acquired at a first projection direction relative to an object of interest and the first frame acquired before the second frame and ii) through a second channel, a third frame acquired at a second projection direction relative to the object;
- an estimator configured to compute from the first frame and the later acquired second frame an estimated interim frame;
- an aligner configured to temporally align the estimated interim frame with the third frame of the second channel;
- an output interface configured to output said estimated frame and third frame as a pair of temporally aligned frames.

According to one embodiment, the third frame is acquired after the first frame and before the second frame. In this embodiment, estimator operates as an interpolator. The estimated frame is interpolated from the first and second frame by using the acquisition time of the third frame The interpolated frame forms an "interim" frame between the acquisition times of first and second frames to "fill" the instance in the first stream as defined by the third frame's acquisition time. In other words, a frame is interposed for an instance where there is no first channel frame acquired. By including the estimated/interpolated frames in the respective channels or streams, the frame pairing effects a "virtual" increase of frame acquisition rate in the first channel.

According to one embodiment, upon receiving a new second channel frame acquired after the second frame, the estimator is configured to compute a new estimated image from the previous third frame and the new second channel frame The aligner configured to align the new estimated or interpolated interim image with the second frame. The output unit outputs the new estimated image and the second frame as a new pair of aligned frames, the apparatus thereby producing a plurality of temporally aligned pairs for the two channels. In other words, the estimated frames computed for either channel are then paired up with the respective frame from the other to so align the streams in time.

According to one embodiment, the apparatus further comprises a motion detector or estimator configured to detect, based on image information in the first and the second frame or in the third frame and the new second channel frame, a movement of the object during acquisition of the first and second frame or during acquisition of the third frame and the new second channel frame, the interpolator using the detected motion, if any, to compute said interpolation.

According to one embodiment, the apparatus operates to estimate or interpolate across time (temporally) from two frames in the same channel. The temporal interpolation uses a combination of motion-estimation and in one embodiment soft-thresholding to achieve an accurate estimate for the interpolated frame from two acquired frames. Because of the aligning in time (temporally aligning) of actual frames and estimated frames, a temporal distance between two (or more) channels can be effectively nullified thereby eliminating or at least reducing artifacts caused by the temporal distance. In the past there were efforts to reduce the temporal distance. However, with the apparatus as proposed herein, even large temporal distances up to 66 ms can be corrected or compensated by the apparatus. The apparatus also allows for example stereoscopic imaging at half the speed of normal (monoscopic) imaging using the same frame-rate and timing to acquire frames. In other words, the benefit of 3D imaging can be harnessed and still the x-ray dosage can be kept as low as for monoscopic imaging. By pairing the estimated or interpolated frame up with the respective frame from the other channel, each frame in a frame pair is treated (by a post-processor such as 3D image combiner or any other post-processor) as if it were acquired at the same time. The pairing may be effected by indexing each estimated frame in a pair with the acquisition time of the other, actually acquired frame.

According to one embodiment, the estimator is configured to morph the estimated or interpolated frame towards the third frame. The apparatus comprises an image merger configured to merge the so morphed estimated frame with the third frame so as to improve a signal-to-noise ratio in the third image or is configured to merge the new interpolated frame with the second frame so as to improve a signal-tonoise ratio in the third image or second frame, respectively. For example, in stereoscopic imaging, frames acquired in the left channel can be used to improve signal-to-noise in the right channel and vice versa. In other words dose-requirement for one- or more channels can be reduced. According to one embodiment motion estimation and soft-thresholding techniques can be used for the merging operation. The morphing operation is similar to the motion based interpolation mentioned earlier but further includes a motion compensation to compensate for the apparent motion of the object caused by imaging the object at the two different projection directions.

According to one embodiment, the image frames in the two channels are alternately acquired.

According to one embodiment, a frame rate in the second channel is less than a frame rate in the first channel. More particularly and according to one embodiment, a refreshing in the second channel to acquire the new second channel frame is triggered by any one of i) the motion detector detecting a motion based on the third frame and a previous second channel frame, said motion exceeding a preset user-adjustable threshold ii) an ECG signal received from the object.

This allows further reducing the x-ray dosage because refreshing in one of the channels is triggered by medical events or other events that are likely to lead to significant patient or object movement. Absent any such motion, one of the channels is not refreshed because no new information is gained. Minor movement however is followed through or tracked in the other channel having the higher frame or refresh rate. In this embodiment, because of the lower refreshing rate in the second channel, there may be no second channel frame acquired between the acquisition times of two consecutive first channel image frames. In this case estimator operates as an extrapolator and uses the motion detector and the respective acquisition times of the received first channel frames to extrapolate to obtain the estimated second channel frames from previous frames in the slow paced second channel.

According to one embodiment the respective frame rates in the two channels are independently user-adjustable to better allow adjusting to the time scales of the object's dynamics.

According to one embodiment, the apparatus further comprises a 3D image processor or combiner configured to process the output frame pair or pairs into a 3D image for display on a 3D capable screen. The apparatus may then be used for stereoscopic imaging. However rather than combing the frames in each pair into a 3D image, other post-processor modules may be used instead or in addition. According to one embodiment a processor for dual-energy imaging is used, where the frame pair is combined to obtain images that allow improved hard tissue-soft tissue differentiation.

According to one embodiment, the first and second channels are two respective channels in any one of i) a stereoscopic imaging system, ii) a bi-plane imaging system, iii) a dual-energy imaging system. According to one embodiment, the stereoscopic or dual-energy imaging system may be bi-plane, so there are two X-ray tubes, one for each projection direction, and two detectors, one for each X-ray tube. In alternative embodiments, a single detector may be used instead.

There may also be a need to improve signal-to-noise ratio in multi-channel imaging system. According to a second aspect of the invention there is provided an image processing apparatus, comprising:

an input interface for receiving i) through a first channel, a first frame acquired at a first projection direction relative to an object of interest and ii) through a second channel, a second frame acquired at a second projection direction relative to the object;

an estimator is configured to morph the first frame towards the second frame to so obtain a morphed frame;

an image merger configured to merge the so morphed frame with the second frame so as to improve a signal-to-noise ratio in the second frame.

This allows using less x-ray dosage as signal-to-noise ratio can be improved by merging with images from the other channel rather than only with images from the same channel. According to one embodiment the first image is additionally merged with one or more frames from the same first channel. Rather than estimating in "time" in each channel separately as is done in the image processing apparatus according to the first aspect of the invention, the imaging apparatus according to the second aspect of the invention is configured to morph across the two channels so effectively morphs across the two different projection angles. In other words according to the second aspect, the estimation to effect the pairing as in the first aspect may not be necessary. Any first channel image can be morphed over (for the purpose of merging) to the second channel image whose signal-to-noise ratio is to be improved. According to one embodiment, the results may be improved by choosing a first channel image that was acquired immediately next or before the second channel frame.

According to an alternate embodiment, cross-channel morphing is supplemented by estimation in the second channel so estimator operates "component-wise" to first extrapolate or interpolate in the first channel "down" in time to the acquisition time of the noisy second channel frame to obtain an estimated first channel frame similar to how it is done above in the first aspect of the invention. Estimator then morphs said estimated first channel frame across to the second channel frame.

Both aspects help reduce dosage on the patient during multi-channel imaging sessions by implementing "trans-channel" approach: information from one channel is used to improve or supplement image information in the other.

Definitions

"Consecutive (first or second channel) frames" means herein that, in the same channel, a later frame is the immediate next to an earlier frame so there is no further frame from the same channel between the two but there is in general (if frame rate in both channels is about equal) a frame in the other channel acquired between the two consecutive (first or second channel) frames.

"Temporal distance" between the two frame streams or channels is the time that elapses between two consecutive frame acquisitions in different channels.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
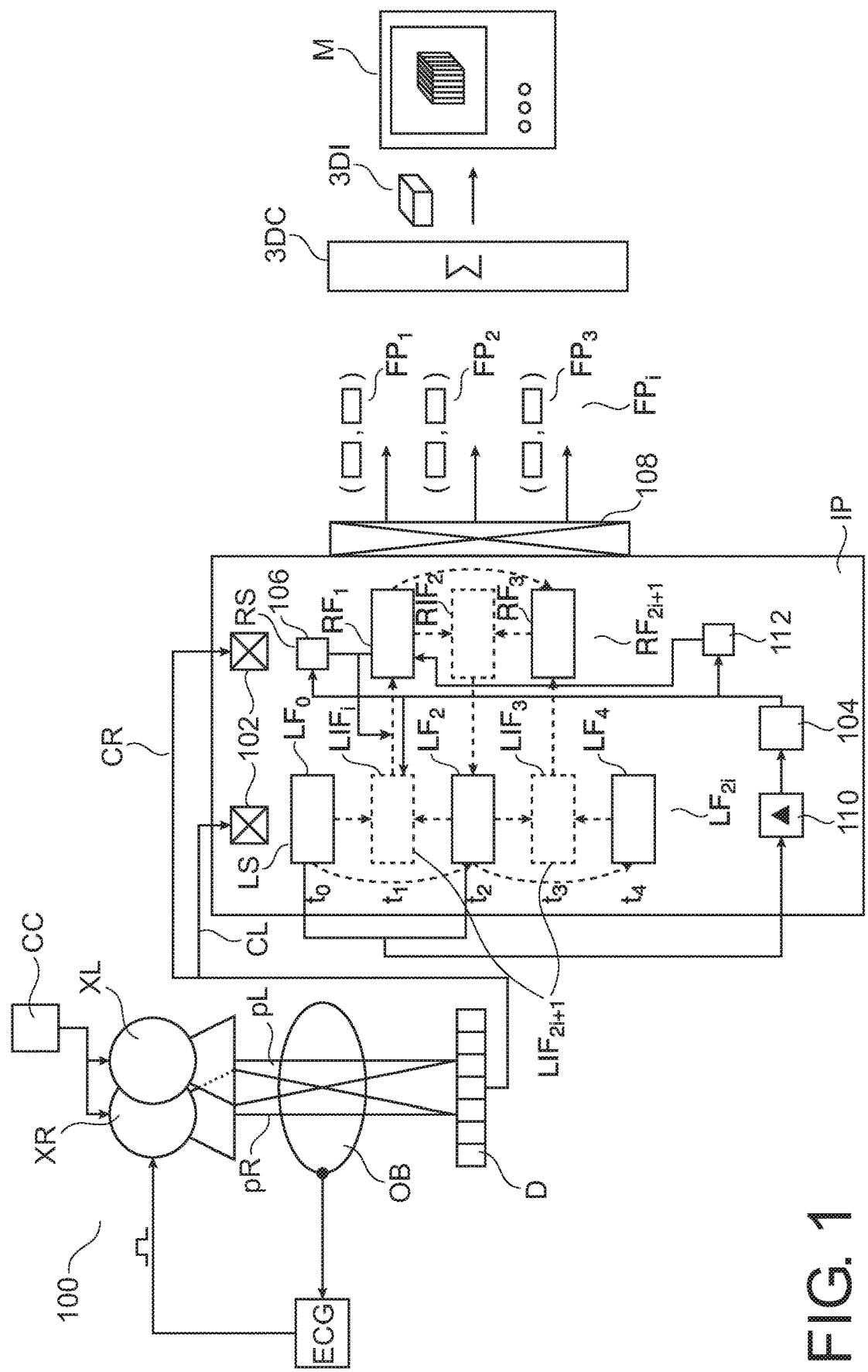
FIG. 1 is an x-ray imaging processing system.

With reference to FIG. 1, a multi-channel x-ray image processing system ("imager") 100 is shown.

In one embodiment the multi-channel imager 100 is a stereoscopic imager with two channels, a right channel CR and a left channel CL. Overall operation of imager 100 is controlled by a computer console CC.

X-radiation comprising x-ray beams pR, pL are emitted from a right x-ray source XR and a left x-ray source XL, respectively. Only one of X-ray sources XR, XL emits their respective x-rays pR or pL at any one time. X-rays pR or pL are then detected by a single detector D after their respective interaction with an object OB. Alternatively there may be two detectors, one for each x-ray source or tube XL, XR if a bi-plane arrangement is used. The two x-ray tubes XL, XR and the one or more detectors are arranged in a frame (such as a c-arm) or gantry (not shown). According to one embodiment, the frame therefore the position of the x-ray tubes XR, XL and the one or more detectors D are assumed stationary during the image acquisitions of both streams. Object OB is positioned on an examination table (not shown) and between any one of the two x-ray tubes XR, XL and detector D. Object OB may be a patient who is positioned relative to the two X-ray tubes XR, XL so that the respective x-rays pR,pL impact on and interact with object OB at a region of interest that is to be examined by a radiologist. When interacting with matter in the object OB, X-ray beams pR and pL are attenuated. The level of said attenuation is dependent on the densities of object material in the respective x-ray's pL, pR in-tissue path as they travel through the object OB. Detector D is made up of a grid of detector cells (not shown) each translating respective parts of the impinging attenuated x-rays pL or pR into electric signals. Said electric signals are then converted by a data acquisition system (DAS—not shown) into respective digital values that are consolidated into a 2-dimensional array forming a projection image for any one exposure by either x-ray beam pR or pL for a given acquisition time. Each projection image is associated therefore with either the left x-ray tube XL or the right XR tube and the acquisition time of said projection image. The digital values are representative of the attenuation level experienced by the respective part of one of the x-rays pR, pL. The images therefore record projection views or "footprints" of the object's anatomic structures having different densities.

A left stream LF or sequence of projection images ("frames") $LF_0$, $LF_2$, $LF_4$ are acquired for x-ray beam pL originating from left x-ray tube XL. Left channel stream LF is then forwarded along left channel CL to an imaging processor IP whose purpose and operation will be explained in more detail below. In a similar fashion, right channel stream RF is acquired for x-ray beam pR originating from right x-ray source XR. Right stream RF is likewise forwarded to said image processor LP via right channel CR. The two frame streams RF, LF are then received by a suitable input unit 102 at said image processor IP. The image information resulting from said processing is then forwarded by output unit 108 to a 3D image combiner 3DC that translates the received image information into 3D image information 3DI which can then be rendered for view on monitor M. A user such as a radiologist may then be able to view a 3D representation of a region of interest of patient OB. According to one embodiment, left and right streams LF, RF are acquired whilst the frame or gantry remains stationary between acquisitions from the different streams LF, RF. As schematically indicted in FIG. 1, the two x-ray sources XR, XL are slightly offset with respect to each other so that respective x-ray beams pR, pL are incident on object OB at different projection directions. Ideally the two x-ray beams irradiate object OB whilst said object OB is in the same spatial configuration. In practice however the two x-ray tubes cannot irradiate the detector at the same time because of the integration time required for the detector's electronics to record each exposure. But even if a biplane arrangement is used, left and right channel are still not acquired at the same time because otherwise Compton scatter of one channel will distort the image on the other channel thereby reducing the signal to noise ratio.

There is therefore a temporal offset or "distance" between any two left and right stream frames. During said temporal offset $t_A$ a spatial configuration of the imaged object OB may very well change so any two consecutive left and right images do not in general record the same configuration or "scene". Said change of spatial configuration may be brought about by the patient moving about or by heart and or breathing activity. However operation of 3D image combiner 3DC rests on the principle that it is indeed the same (internal) spatial configuration of OB that is recorded by any two consecutive left and right images. The spatial change in configuration between two consecutive left channel and right channel frames $LF_i$, $RF_{2i+1}$ causes image artifacts in the combined 3D image 3DI output by 3D image combiner 3DC.

Because no two left channel and right channel frames $RF_{2i+1}$, $LF_{2i}$ can be acquired at the same time, the two image streams RF and LF are misaligned in time ("temporal misalignment"). In other words, there is at least one frame in one stream RF, LF that has been acquired when no other frame was acquired in the other stream LF, RF. An example of temporal misalignment is shown in FIG. 1 where no two frames, each from different streams, have the same acquisition time. This case of temporal misalignment is the result of an image acquisition protocol where frames in the streams are acquired in alternate succession as exemplary shown in FIG. 1 for one embodiment. This temporal misalignment is indicated graphically in FIG. 1 by the two streams RF and LF shown in a staggered fashion. The two streams RF and LF are acquired sequentially but alternately across the two channels CL, CR.

Broadly speaking, image processor IP as proposed herein helps to essentially nullify or eliminate temporal misalignment or temporal distance between the two streams LS, RS. Image artifacts in the reconstructed 3D image 3DI may thereby be reduced.

Operation

Image processor IP is communicatively coupled to imager 100 via left and right channels CL, CR to respectively receive left stream and right stream RF, LF at a suitable input unit 102. Each frame $RF_{2i+1}$, $LF_{2i}$ is assumed to be indexed by i) its individual acquisition time as shown schematically as $t_0$-$t_4$ in FIG. 1 and whether it is a left or right channel frame. This information may be derived from meta-data incorporated in each of the frames $RF_{2i+1}$, $LF_{2i}$ or may be requested by input unit 102 from imager 100 or from a database where this meta-data is held.

In one embodiment, the received frames $RF_{2i+1}$, $LF_{2i}$ are stored in a suitable data structure and said data structure is then updated as new frames are received at the input unit. The data structure holds the indexed frames ordered in a sequence according to their acquisition time. It may be understood that rather than storing the frames themselves in the data structure suitable references may be stored instead that allow the image processor IP to retrieve the respective frames from a data base (not shown).

An estimator 104 then reads in any two consecutive left channel frames $LF_{2i}$, for example $LF_0$ and $LF_2$ to estimate therefrom a left channel interim image $LIF_1$. According to one embodiment, estimator 104 includes a motion detector 110. Motion detector 110 uses image information in each of the consecutive temporal neighbor images $LF_0$ and $LF_2$ to estimate a motion vector describing the motion that the object OB has undergone throughout the period in between acquisition times $t_0$ and $t_2$ of the respective left channel frames $LF_0$ and $LF_2$. Motion detector 110 may operate based on block matching algorithms with or without soft-thresholding or may operate based on optical flow techniques.

In block matching according to one embodiment, each of the consecutive left frames $LF_0$ and $LF_2$ are segmented into blocks of n-by-n pixels. The image portions or blocks in each of the two frames are then compared and matched up across the two frames according to pixel values or shapes of image portions in the blocks. Matching image portions that are determined similar are assumed to be footprints of one and the same anatomic structure of object OB. The two left frames $LF_0$ and $LF_2$ are then registered along a common coordinate system. The motion estimation is performed by computing for each block in one frame $LF_0$ a motion vector by searching for a best match in a corresponding neighborhood in the other frame $LF_2$ to so effect the block-matching. For the matching, a rigid or non-rigid linear transformation can then be computed to map one block of one frame $LF_0$ into a block of the other frame $LF_2$. The result is a 2D array of motion or displacement vectors, which are then used for the estimation or interpolation. The 2D array of motion or displacement vectors define a dynamic transformation that describes the dynamics of the object OB The transformation describes the shift and/or expansion or contraction of the respective anatomic structure and thus the spatial configuration change of object OB in the period $t_0$ though $t_2$ between the respective acquisition times. In other words the dynamics of the object OB or the region of interest can thereby be estimated. Estimator 104 then establishes by look-up operation in the data structure the acquisition time $t_1$ of a right channel frame $RF_1$ that was acquired between the acquisition times of the left channel frames $LF_0$ and $LF_2$. The computed transformation is then applied to the earlier one $LF_0$ of the two consecutive left channel images $LF_0$ and $LF_2$ and said transformation is then evaluated at the desired interim right channel frame instant $t_1$ to so compute interim left channel frame $LIF_1$. In one embodiment, the proportions of the interim period $t_1$-$t_0$ and $t_1$-$t_2$ are compared and the transformation is than applied proportionately to earlier frame $LF_0$. For instance, if $t_1$-$t_0$=$t_1$-$t_2$, the displacement vectors are scaled by 0.5 to half their length and it those scaled vectors that are then applied to the first frame $LF_2$ to arrive at the interpolated left channel frame $LIF_1$. Alternatively, with reversing directions of the respective vectors, the dynamic transformation may also be applied to the later frame $LF_2$ to thereby effect a backwards interpolation rather than a forward interpolation. In other words interim left channel frame $LIF_1$ is an estimate for a frame as it would have looked like had it been acquired by using the left hand x-ray source XL at interim time $t_1$ when no left channel image was actually acquired. In yet other words, for the case of two consecutive left channel images $LF_{2i}$, $LF_{2(i+1)}$ (i=1,2,...) where the right channel frame $RF_{2i+1}$ is acquired in between the respective acquisition times $t_{2i}$, $t_{2i+1}$ of the two consecutive left channel frames $LF_{2i}$, $LF_{2(i+1)}$ (i=1, 2,...), estimator 104 operates as a dynamic interpolator to compute interim left channel frame $LIF_{2i+1}$ for pairing same up with right channel frame $RF_{2i+1}$. Motion detector 110 operates in a completely analogous manner to compute the respective interim right channel frames $RIF_{2i}$.

The above described operation of image processer may also be applied if, according to a different acquisition protocol, not one but a plurality of left channel images are acquired in one "block" over a period of time and imaging system only then switches over to the right channel and likewise acquires a block of right channel frames and so forth. In other words, imager 100 may not alternate from one X-ray tube XR, XL to the other channel after a single acquisition as shown in FIG. 1, but switch-over to the other X-ray tube XR, XL occurs after a plurality of acquisitions per channel CR, CL. In this block acquisition embodiment, the previous interpolation is applied in the same manner as described but now there are a plurality of interpolations one for each of the acquisition times of frames in for example the right channel frame block that has been acquired in between the two temporal neighbor blocks of first channel frames.

An aligner 106 then aligns or associates actually acquired frame RF1 and said interpolated interim frame $LIF_1$ to form a frame pair that is aligned in time. Said pair is then indexed by the interim time $t_1$ and is then forwarded to 3D image combiner 3DC. Combiner 3DC then combines the image information from the aligned pair and processes same as they were acquired at the same time and generates a view or image 3DI of object OB at the indexed instance $t_1$. In this manner the temporal distance between the right channel frame $RF_1$ and the two left hand images $LF_0$ and $LF_2$ is compensated or eliminated.

The above computations are repeated for each consecutive left channel frames $LF_{2i}$, $LF_{2(i+1)}$ (i=1,2,...) to compute the sequence of respective interim left channel frames $LIF_{2i+1}$ (i=2,3,...) that are then paired up with the respective right channel frame $RF_{2i+1}$. A completely analogous operation is applied by interpolator 104 and aligner 106 to the right channel images $RF_{2i+1}$ to compute a sequence of interpolated right channel interim images $RIF_{2i}$. Each of said right channel interim frames $RIF_{2i}$ is then aligned by aligner 106 with the respective left channel frames $LF_{2i}$ that was acquired between the acquisition times of the respective two right channel frames $RF_{2i+1}$, $RF_{2(i+1)+1}$, (i=0,1,2). A completely analogous operation of estimator 104 and aligner 106 is carried out for the "block" acquisition embodiment mentioned earlier.

In other words image processor IP operates to produce a sequence of frame pairs $FP_i$ effectively "interleaving" the two image streams by using interpolated or estimated frames in each stream to fill in the respective "time gaps" to so bring about alignment in time between the two streams.

According to one embodiment image processor IP operates in "real-time" that is the respective interpolated frame in either channel is computed upon receipt of a new frame in the other channel.

According to one embodiment image processor IP may also operate in a delayed buffer mode in which first a pre-set number of frames in each channel is received and the computations above are then carried out on the sub-sequence of buffered frames.

According to one embodiment the interpolator 104 and aligner 106 operate to compute the respective interpolated frames and their aligning by alternating between the two streams. In an alternative embodiment estimator 104 operates first on a sequence of frames in one channel and then switches over to operate on a sequence of frames in the right stream.

According to one embodiment a "refreshing" or frame acquisition rate in each channel can be set separately and independently. In one embodiment, this functionality can be provided by the control console CC that is used to control the operation of imager 100. Yet more specifically according to one embodiment the refreshing rate in one channel is lower than in the other. For example the refreshing rate of the right x-ray tube XR serving right channel CR, is set lower than the refreshing rate of the left x-ray tube XL serving the left channel CL. Specifically and according to one embodiment, the refreshing in the right channel is made contingent on certain events. According to one embodiment that event is an ECG signal which is acquired from the object OB via an ECG acquisition unit. In this manner right hand channel CR refreshes only if a desired heart cardiac phase is observed at object OB. In this manner the dosage on the patient can be kept low because the acquisition of images in between two of the desired cardiac phases may not add any new information because the patient has remained relatively stationary. In this unequal frame rate embodiment there may be no right channel frame acquired between the respective acquisition times of two consecutive left channel frames because of the higher frame rate of left channel compared to right channel frame rate. In this case estimator 104 operates as an extrapolator and uses the dynamic information gained from previous right channel frames to "predict" how the latest available right channel frame may have looked like had it been acquired by right x-ray tube XR at the respective acquisition times of the faster paced left channel frames. In this embodiment, motion estimator 104 operates in a similar manner as described above in connection with the interpolation mode. In other words motion estimator computes a dynamic transformation describing the dynamics between two or more previous right channel frames: Said transformation is then applied to the latest right channel frame and is then evaluated at instances defined by the acquisition times of the left channel images meanwhile received via the faster paced left channel. In this manner the predicted right frames are produced and output. However, as soon as right channel is refreshed and a new right channel frame is acquired, estimator 104 establishes which two left channel frames have been acquired immediately before and after said newly received right channel frame, and estimator 104 then reverts to interpolation mode as described above and computes an interim left channel frame for the newly received right channel frame. In either case of extrapolation or interpolation, aligner 106 pairs up the left channel frames with the respective predicted right channel frame or pairs up the newly received right channel frame with the interpolated interim left channel frame and output unit 108 outputs the so computed frame pairs to 3D image combiner 3DC.

Alternatively and if no real-time operation of image processor is desired or needed by the user, according to one embodiment image processor IP is capable of operating in a buffer mode. In this mode, frames in the faster left channel are accumulated in a buffer. When slower channel eventually does refresh and when the new right frame is received at input unit IU, estimator 104 operates in interpolation made and computes based on the newly received right channel and on the previous right channel image, the one or more interpolated interim right channel frames, one for each of the buffered left frames, and aligner then pairs same up as previously described. The frame pairs are then forwarded via output unit OU to 3D image combiner 3DC. According to one embodiment, even when operating in real-time mode the buffer operation may still be used to reality check the previously computed pairs having the predicted frame. The user may than "scroll back in time" and compare the previously computed 3D image with the re-computed once based on the pairs now including the interpolated frames rather than the previous predicted ones.

According to one embodiment the image processor IP also comprises a merger 112 and operates as a signal-to-noise-ratio "booster" configured to improve the signal to noise ratio for any given frame in either the left channel CL or right channel CR. According to one embodiment, merger uses soft thresholding to improve signal to noise ratio. When integrating or merging any two frames, pixels are only integrated or merged if a difference ("delta") in the grey level between the pixels of the two image frames is within a certain threshold. The value of said threshold can be a static value but may also be determined by measuring the amount of noise in the image. Assuming that the frame whose signal-to-noise ratio is to be improved (referred herein after as the "noisy frame") is a left channel frame $LF_{2i}$, merger 112 operates according to one embodiment to merge image information of the noisy frame with a frame or frames in the same channel. Additionally or instead, the proposed image processor IP is configured to also merge the noisy frame with image information from other right channel frames of the other channel and in particular with the interim interpolated right channel frame $RIF_{2i}$ with which the noisy frame has been pair up with. In other words, image processor is capable of enlarging the available pool of frames which can be used for merging thereby allowing more image information to be used thus increasing signal-to-noise ratio. The merging operation retains image portions and information that are sufficiently similar and rejects and/or averages out information that is not. Information content across the left and right channels images that are sufficiently similar have a higher fidelity and are attributable to useful ("payload") signals rather than to noise. When merging, estimator operates in morphing mode to morph the to-be merged frames from the other channel towards the noisy frame.

In one embodiment, to achieve morphing from left channel frame to right channel frame, estimator operates in extrapolation mode and now operates additionally to compensate for the "virtual" motion of the segmented image portions or blocks across the detector's plane caused by and corresponding to the offset between the X-ray tubes XR and XL. In similar fashion morphing can be effected the opposite way from right channel frame to left channel frame. In other words the morphed frame is an estimate how the frame acquired at the desired time may have looked like had it been acquired by the other x-ray tube XL, XR, respectively. Said angular or lateral offset of the X-ray tubes XR, XL is part of the imaging geometry that can be derived from the metadata in the frames or it can be directly requested from imager 100 or retrieved from a database. Although image processor may operate to morph over any one of the right channel frames for merging same with noisy left channel frame, a higher or better signal-to-noise ratio results may be achieved by morphing over the interpolated frame that has been paired up with the noisy image because said interpolated image is likely to be similar to the noisy image so the separation between noise and true signal can be easier accomplished.

According to one aspect, image processor IP may still operate without the aligner 106 but the merger 112 to only improve signal-to-noise ratio of any frame in one of the channels by morphing "over" any user specifiable frame or frames from the other channel and merging same with said noisy frame. In this embodiment, no aligning step is carried out and no interpolated interim frame is computed by estimator 110.

In FIG. 1 the two channels CR and CL are shown to separately feed into image processor IP. However this is only an exemplary embodiment. According to another embodiment there is a single channel feeding into image processor IP and respective left and right frames originating respectively from exposure by left or right x-ray source XR XL are resolved into the two respective channels at input unit 102 by a suitable switch scanning the frames' meta-data.

According to further embodiments imager 100 may not include the two separate x-ray tubes XR, XL as shown in FIG. 1 but a single x-ray tube with a movable focal spot or two different focal spots and the two channels correspond to frames taken when the focal spot is the respective one of the two positions or when the respective one of the two spots is used. WO2010/146504 describes an x-ray tube capable of generating two focal spots displaced relative to each other, each spot generating x-ray beams having different projection directions. In yet other embodiments each channel may correspond to a single or a number of x-ray tubes operating at different energy (keV) levels.

It will be appreciated that in the above there is nothing peculiar about the left or right channel. It is merely for the sake of definiteness and clarity that the various modes of operation and embodiments of image processer IP have been explained mostly with reference to the left channel. The same applies mutatis mutandis to the right channel and its frames and it may also be appreciated that in some embodiments is the left channel that has the lower frame rate and the right channel is the faster paced channel.

According to one embodiment image processor IP can operate in a "leapfrog" mode. In other words rather than operating on any two consecutive frames in either channel, image processor can be configured to effectively skip a selectable number of frames per channel which frames are not considered by image processor IP and left out of consideration. For example in one embodiment IP image processor may be configured to operate on any other or any j-th frame (j>3) so operates effectively on a true subsequence in the respective left or right stream of frames. According to one embodiment, image processor allows leap frog mode operation in either channel CR, CL or both channels CR and CL as desired for the instant session or image acquisition run.

In some embodiment imager may operate across more than 2 channels for example 3 channels so the above is not restricted to stereoscopic imaging. In the 3 channel embodiment image processer IP may operate to output triplets across the three channels that are aligned in time. In yet other 3 or more channel embodiments, image processor may operate to output aligned pairs of frames for any combination or selection of two channels from the 3 and more channels.

In one embodiment 3D combiner 3DC may be arranged as a separate module from image processor IP. Combiner 3DC may be part of an existing stereoscopic imaging system in which image processor may be included in same as an add-on. In an alternative embodiment, combiner 3DC is included as part of image processor IP. According to one embodiment, image processor IP may be arranged as a dedicated FPGA or as hardwired standalone chip or may run as module on console CC. Image processor IP may be programmed in a suitable scientific computing platform such as Matlab® or Simulink® and then translated into C++ or C routines maintained in a library and linked when called on by central operation console CC.

Figure 2:
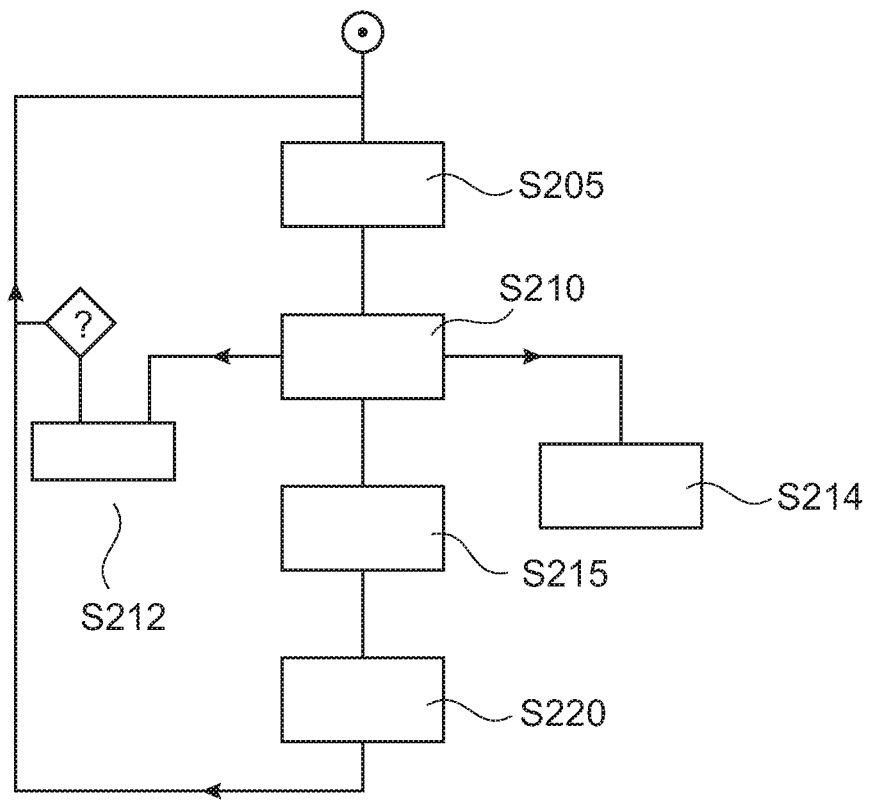
FIG. 2 is flowchart of a method of image processing.

Referring now to FIG. 2, a flowchart is shown for a method of image processing underlying operation of above image processor IP.

At step S205 two frames are received through a first channel, one frame acquired after the other. Both first channel frames have been acquired from an object along a first projection direction by an x-ray tube-detector arrangement. There is also received at least one image or frame through a second channel acquired from the object at a second projection direction different from the first projection direction.

At step S210 an estimated frame is computed from the two first channel frames. According to one embodiment, the second channel frame is acquired after the earlier first channel frame and before the later first channel frame. In this embodiment, the estimation is an interpolation using the acquisition time of the second channel frame and the estimated frame is an interim frame interposed in time between the two first channel frames.

At Step S215 said estimated frame is then aligned with the second channel frame.

At step S220 the estimated frame and the second channel frame are output as a temporally aligned pair of frames.

According to one embodiment, the pair of aligned frames can then be input in a 3D image processor to produce an instantaneous 3D view corresponding to the acquisition time of the second channel frame and said pair can then be rendered for display on a 3D capable screen of for view with dedicated 3D goggles. Previous steps S210-S220 are repeated for each newly in-coming and received first channel frame and the latest available first channel frame acquired before the newly received first channel frame. In other words according to one embodiment, steps S210-S220 are repeated for any two consecutive first channel frames and any second channel frame acquired between the two. The so computed interim frames are each respectively paired off with the respective second channel frame acquired in between the respective two consecutive second channel frames. In this manner a stream of paired first and second channel frames is produced which is continuously updated with each incoming frame. In this manner, a corresponding update of the displayed 3D image can be effected by 3D processing each frame pair sequentially as they are output.

According to one embodiment steps S210-S220 can also be applied conversely on any two consecutive second channel frames to obtain estimated (interim) second channel frames and to pair said second channel interim frames with the corresponding first channel frames that have been acquired between the respective second channel frames.

According to one embodiment, the earlier first channel frame is the latest of all first channel frames acquired before the second channel frame and the later first channel frame is the earliest of all frames acquired after the second channel frame. The earlier and later first channel frames are the immediate temporal neighbors of the second channel frame. Similarly the consecutive second channel frames are immediate neighbors of the respective first channel frames. However, according to another embodiment the method may also be applied in a leap frog manner to first channel frames that are not acquired immediately before or after the second channel frame. Again, same applies mutatis mutandis to the second channel frames that may not be immediate temporal neighbors of the first channel frame.

By operation on of above methods, both streams in the respective channels are effectively aligned because temporal gaps in one channel between two consecutive frames are "filled" by the interpolated frame.

The above method may also be applied to a three (or more) channel system. In this embodiment, frame triplets rather than frame pairs are output at step S220. According to an alternative embodiment, the above described operation is performed for any two channels from the three channels.

According to one embodiment, estimation step S210 includes a step of motion detection at step S212. In said motion detection step S212 a motion of the imaged object is detected that occurred during acquisition of the two consecutive frames. The so detected motion is then used to compute the interpolated interim frame by applying the same motion to the earlier frame or by applying a reversal of said motion to the later frame and by evaluating said motion at the acquisition time of the right channel frame.

According to one embodiment the refreshing rate of the second channel is contingent on whether or not a motion is detected between the two consecutive frames. If a motion is detected and using a threshold said motion is determined to be beyond said threshold, a refresh request is issued to the effective x-ray tube so that a new second channel image is acquired. In this embodiment it is only the frames in the first image that closely follow the motion of the object and said information is supplemented only occasionally by right channel images if the motion observed between two consecutive first channel frames is deemed significant enough to warrant such a second refreshment and hence dosage exposure. According to one embodiment, the threshold to measure the extent of the motion is the displacement measured in pixels by the respective displacement or motion vectors computed in the motion estimation step S212. Said vectors measure the change in spatial configuration of the object as evidenced by shift, rotation, contraction or expansion of related image portions across the two consecutive frames when registered along a common coordinate axis.

According to one embodiment, refreshment of the second channel may be triggered by a received ECG signal representing for example a cardiac phase of the object. In other embodiments other signals (such as signal indicating object's breathing cycle) may be received that are indicative to a spatial configuration of said object or patient.

When the frame rate in the second channel is lower than in the first channel, a situation may occur where there is no second channel frame acquired in between the acquisition times of the two consecutive first channel frames. In this case, above estimation step S210 is implemented as an extrapolation step. In one embodiment, a motion detection is applied to the latest and previous second channel frames. Said motion is then applied to the latest second channel frame and the frame is extrapolated to the respective acquisition times of the two first channel images. The so predicted second channel frames are then paired up with the respective first channel frames to so effect alignment in this unequal frame rate embodiment.

According to one embodiment there is also a step S214 of merging the respective estimated interim frame computed for any one of the two channels channel with a frame of the other channel. A signal-to-noise ratio can thereby be improved in the other channel. In one embodiment this step includes morphing the interpolated frame over to the other channel. In one aspect said merging and morphing step S214 to effect signal-to-noise-ratio enhancement may be carried out without the aligning step and even without the estimation of the interim frame. When no interim frame is estimated, any frame from one channel may be morphed over using the lateral or angular offset between the projection directions to compensate for an apparent motion caused by said offset and/or using a motion estimation using previous frames in the same channel of the frame to be morphed.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing system, comprising:
a multi-channel X-ray imager for supplying a first stream of frames from a first channel acquired at a first projection direction based on X-rays emitted at first times from a first source relative to an object of interest; and
a second stream of frames from a second channel acquired at a second projection direction based on X-rays emitted at second times, different from the first times to avoid temporally overlapping the first times, from a second source relative to the object;
an input interface for receiving
i) from the first stream, a first frame acquired at a first acquisition time and a second frame acquired at a second acquisition time after the first acquisition time;
ii) from the second stream, a third frame acquired at a third acquisition time after the first acquisition time and before the second acquisition time;
a motion detector configured to detect a motion of the object during acquisition of the first frame and second frame, and to determine a transformation between the first frame and the second frame, the determined transformation describing the motion of the object from the first acquisition time to the second acquisition time;
an estimator configured to apply the determined transformation to the first frame to compute from the first frame and the second frame an estimated frame of the first stream corresponding to an acquisition time temporally between the first and second acquisition times, wherein refreshing the second stream to acquire a fourth frame from the second channel is triggered by the detected motion exceeding a threshold;
an aligner configured to temporally align the estimated frame of the first stream with the third frame of the second stream to form a corresponding frame pair comprising the estimated frame and the third frame temporally aligned in time;
an output interface configured to output the frame pair; and a screen for displaying images based on at least the frame pair.

2. The image processing system of claim 1, wherein the estimator computes the estimated frame by interpolating between the first and second frames using the third acquisition time.

3. The image processing system of claim 1, wherein the input interface further receives from the second stream the fourth frame acquired at a fourth acquisition time after the second acquisition time, the estimator is configured to compute a new estimated frame from the third frame and the fourth frame corresponding to an acquisition time temporally between the third and fourth acquisition times, the aligner is further configured to temporally align the new estimated frame of the second stream with the second frame of the first stream to form a new corresponding frame pair comprising the new estimated frame and the second frame temporally aligned in time, the output interface is further configured to output the new frame pair, thereby producing a plurality of temporally aligned frame pairs for the first and second channels.

4. The image processing system of claim 1, wherein the first and second frames from the first stream are alternately acquired with the third frame from the second stream.

5. The image processing system of claim 1, wherein the refreshing the second stream to acquire the fourth frame from the second channel is further triggered by receiving an ECG signal acquired from the object of interest via an ECG acquisition unit.

6. The image processing system of claim 1, wherein respective frame rates in the first stream and the second stream are independently user-adjustable.

7. The image processing system of claim 1, further comprising a 3D image processor configured to process the output frame pair into a 3D image for display on a 3D capable screen.

8. The image processing system of claim 1, wherein the first and second streams correspond to two respective channels in any one of i) a stereoscopic system, ii) a bi-plane imaging system, iii) a dual-energy imaging system.

9. A method of image processing, comprising: receiving, through a first channel, a first frame acquired at a first acquisition time, and a second frame acquired at a second acquisition time, occurring temporally after the first acquisition time, the first and second frames both being acquired at a first projection direction based on X-rays emitted at first times from a first source relative to an object of interest; receiving, through a second channel, a third frame acquired at a third acquisition time, occurring temporally after the first acquisition time and before the second acquisition time, the third frame being acquired at a second projection direction based on X-rays emitted at second times,
different from the first times to avoid temporally overlapping the first times, from a second source relative to the object of interest different from the first projection direction;
detecting a motion of the object during acquisition of the first frame and second frame, and to determine a transformation between the first frame and the second frame, the determined transformation describing the motion of the object from the first acquisition time to the second acquisition time;
estimating an estimated frame of the first channel by interpolating between the first frame and the second frame, using the third acquisition time and the determined transformation applied to the first frame;
aligning at the third acquisition time the estimated frame of the first channel with the third frame of the second channel to form a corresponding frame pair comprising the estimated frame and the third frame temporally aligned in time; refreshing the second stream to acquire a fourth frame from the second channel when the detected motion exceeds a threshold;
and outputting the frame pair.

10. The method of claim 9, further comprising:
receiving the fourth frame through the second channel acquired at a fourth acquisition time after the second acquisition time;
estimating a new estimated frame from the third frame and the fourth frame;
aligning at the second acquisition time the new estimated frame with the second frame of the first channel to form a corresponding new frame pair comprising the new estimated frame and the second frame temporally aligned in time; and
outputting the new frame pair.

11. A non-transitory computer readable medium having stored thereon software instructions that, when being executed by a processor, performs the method of claim 9.

12. The image processing system of claim 1, further comprising an image merger, wherein the estimator is further configured to morph the estimated frame towards the third frame to provide a morphed estimated frame compensating for a difference between the first projection direction of the first source and the second projection direction of the second source when acquiring the first stream of frames and the second stream of frames, respectively, and wherein the imaging processing system, and wherein the image merger is configured to merge the morphed estimated frame with the third frame to improve a signal-to-noise ratio in the third frame.

13. The image processing system of claim 1, wherein the threshold is user-adjustable.

14. The image processing system of claim 1, wherein a frame rate in the second stream is less than a frame rate in the first stream.

15. The method of claim 9, further comprising:
morphing the estimated frame towards the third frame to provide a morphed estimated frame to compensate for a difference between the first projection direction at which the first and second frame are acquired and the second projection direction at which the third frame is acquired; and
merging the morphed estimated frame with the third frame to improve a signal-to-noise ratio in the third frame.

16. The method of claim 9, wherein the threshold is user-adjustable.

17. The method of claim 9, wherein a frame rate in the second stream is less than a frame rate in the first stream.

* * * * *